United States Patent [19]

Chakrabarti

[11] 3,941,817

[45] Mar. 2, 1976

[54] TERTIARY AMIDE AMPHOTERIC SURFACE ACTIVE AGENTS AND PROCESS FOR THEIR MANUFACTURE

[75] Inventor: Paritosh Mohan Chakrabarti, Wayne, N.J.

[73] Assignee: GAF Corporation, New York, N.Y.

[22] Filed: Sept. 3, 1974

[21] Appl. No.: 502,637

[52] U.S. Cl. ............ 260/404.5; 252/356; 260/408; 260/561 R; 424/70
[51] Int. Cl.² ...................................... C07C 102/06
[58] Field of Search ............ 260/561 R, 408, 404.5; 424/70

[56] References Cited
UNITED STATES PATENTS

| | | | |
|---|---|---|---|
| 2,961,451 | 11/1960 | Keough | 260/404.5 |
| 2,970,160 | 1/1961 | Walker | 260/404.5 |
| 3,122,504 | 2/1964 | Wedell | 260/404.5 |
| 3,257,436 | 6/1966 | Lindner | 260/404.5 |
| 3,262,951 | 7/1966 | Katz | 260/404.5 |
| 3,324,179 | 6/1967 | Scholz | 260/561 R |
| 3,468,639 | 9/1969 | Lindstrom | 260/404.5 |
| 3,468,904 | 9/1969 | Kritchevsky | 260/404.5 |

*Primary Examiner*—Helen M. McCarthy
*Attorney, Agent, or Firm*—Walter C. Kehm; James N. Blauvelt

[57] ABSTRACT

Improved amphoteric surface active agents are obtained from tertiary amides that have been formed by condensation of esters of fatty acids with an aminoalkyl alkanolamine, e.g., aminoethyl ethanolamine, under special conditions, by conventional carboxymethylation with $ClCH_2CO_2Na$ or $ClCH_2CO_2H$. The resultant amphoteric surface active agents are especially useful as wetting agents, forming agents, emulsifiers, etc., and in the manufacture of improved shampoos.

19 Claims, No Drawings

TERTIARY AMIDE AMPHOTERIC SURFACE ACTIVE AGENTS AND PROCESS FOR THEIR MANUFACTURE

BACKGROUND OF THE INVENTION

1. Field of the Invention

This invention relates to the production of novel amphoteric surface active agents formed from novel tertiary amides and thermodynamically and kinetically controlled processes for the manufacture of each of these. The tertiary amides of this invention are therefore useful intermediates in the production of the present amphoteric surfactants, which themselves are useful for a variety of purposes including, e.g., the manufacture of improved shampoos, wetting agents, antistatic agents, detergents, emulsifiers, hard surface cleaners, lubricants, etc. The tertiary amides of the invention are derived by condensation of esters of fatty acids with aminoalkyl alkanolamines and generally are characterized by the formula:

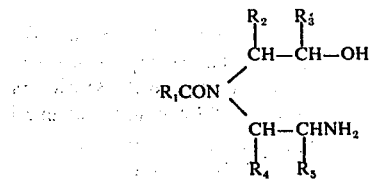

wherein:

$R_1$ is a hydrocarbon radical having from five to twenty-nine carbon atoms, and, when substituted, contains such typical substituents as Cl; Br; OH; or OAlkyl such as $OCH_3$; and $R_2$, $R_3$, $R_4$ and $R_5$ are each hydrogen or unsubstituted or substituted aliphatic hydrocarbon radicals having from one to four carbon atoms which, when substituted, have the same substituents as defined in $R_1$ above.

2. Description of the Prior Art

The production of amphoteric surfactants by reacting fatty amides of hydroxy diamines such as aminoalkyl alkanolamine with monohalocarboxylic acids is disclosed, for example, in U.S. Pat. Nos. 2,961,541 and 2,970,160. However, the amides there disclosed are secondary amides as are those typically prepared by condensation of a fatty acid with an aminoalkyl alkanolamine, such as is disclosed in U.S. Pat. No. 2,344,260. This latter reaction is normally carried out in the range of 130° to 200° C, and even after a prolonged period of heating gives conversions only on the order of 60 to 75%, unlike those of the present invention wherein conversions of 90% or higher are achieved.

Heretofore, amphoteric surface active agents of improved characteristics have not been made from tertiary amides, in large part because amide surfactants have conventionally been prepared from secondary amides. The present invention now is able to fill these voids and permit the production of superior surface active agents.

It is therefore a primary object of this invention to provide useful amphoteric surfactants containing tertiary amide groups for example by condensation of novel tertiary amides with a monohalocarboxylic acid or suitable salt thereof. Such surfactants, because of their unique structural features, offer properties which lend themselves to new and improved surfactant compositions useful, for example, in a number of ways as indicated above.

SUMMARY OF THE INVENTION

The novel amphoteric surface active agents of this invention are essentially derived from novel tertiary amides, which latter compounds are obtained by reacting a fatty acid ester of a lower alcohol or a suitable polyol such as glycerol with a hydroxy diamine such as an aminoalkyl alkanolamine, e.g., an aminoethyl ethanolamine. Thereafter, the resultant tertiary monoamide is condensed with a suitable carboxymethylating agent such as a monohalocarboxylic acid or a suitable salt thereof to form the aforesaid amphoteric surface active agents of this invention.

DESCRIPTION OF THE PREFERRED EMBODIMENTS

The formation of the tertiary monoamide is preferably effected by reacting an aminoalkyl alkanolamine, a preferred aminoalkyl alkanolamine being 2-hydroxyethyl ethylenediamine, hereinbefore or hereinafter referred to as "aminoethyl ethanolamine," with a fatty acid ester in the presence of a basic catalyst such as an alkali metal or a hydroxide or alkoxide thereof at temperatures on the order of 60° to 120° C, preferably between 80° – 100°C. It is to be noted that pressure in itself is not a critical parameter in the present invention and that, under the preferred temperature range, the final product is essentially a tertiary amide. The reaction to form the desired tertiary amide is generally complete in less than 30 minutes.

While the reaction could be carried out at higher temperatures than those indicated above, it must be carefully recognized that, under such conditions, the reaction would have to be arrested as the tertiary amide was formed so as to prevent its rearrangement to the secondary amide, a result normally obtained under such conditions either during prolonged heating, or at higher temperatures.

The reaction, particularly between esters and the aminoalkyl alkanolamine, under base catalysis, takes place rapidly, as well as at low temperatures, and frequently requires only a few minutes for completion. Preferably, this reaction is thermodynamically and kinetically controlled by conventional means well known to those skilled in the art.

It is noted that the present invention, in contradistinction to the prior art, does not need or utilize fatty acids, which is what the prior art has conventionally used, to form secondary amides, but instead utilizes the esters of such fatty acids, thereby obviating the need for stainless steel equipment, as would be required by the fatty acids per se.

Generally, the reaction time ranges between five minutes and one hour, and conversion is greater than 90%.

The fatty acyl moiety in the tertiary amides of this invention can be saturated or unsaturated, substituted or free from substitution and can vary in carbon length generally from about 6 carbon atoms to 30 carbon atoms. Moieties of $C_5$ and of lesser carbon number would not give the requisite detergent properties and moieties of $C_{31}$ and higher would be inadequate in terms of their surfactant properties. Suitable substituents for the present substituted tertiary amides of this invention would include Cl, Br, OH, OCH₃, etc.

As indicated above, the esters of the fatty acids are preferred and, in particular, esters such as those of caproic caprylic, capric, lauric, myristic, palmitic, stearic, arachidic and behenic acids. These esters may also be present in the form of mixtures, particularly those derived from natural fats and oils. In general, for commercial practice, it is recognized that surfactants are not generally available in suitable supply in the pure state but rather in the form, almost always, of mixtures, but this in no way should be considered to detract from this invention.

As indicated above, the fatty acid moiety is supplied as an ester and particularly as an ester of a lower $C_1$–$C_6$ monoalkanol, such as methyl alcohol, ethyl alcohol, tertiary butyl alcohol, or a polyalkanol such as glycerol and the like. Fatty acid triglycerides, particularly those which are natural fats and oils, are particularly suitable. Such triglycerides can be of vegetable origin, such as coconut oil, linseed oil, olive oil, palm oil, peanut oil, tung oil, rapeseed oil, or they can be of animal or marine origin, such as lard, tallow, sardine oil, etc. The natural fats and oils, above described, can be used as such or they can be hardened by hydrogenation before use. Generally, when the ester is a monoalkanol it is customary to remove the alcohol formed during the condensation by distillation, if necessary, under reduced pressure during the course of the reaction. Where, however, the ester is, for example, a triglyceride, the glycerol formed can be allowed to remain in the reaction product, owing to its high boiling point. Preferred aminoalkyl alkanolamines which are suitable for reaction to form tertiary amides in accordance with the present invention generally are of the formula:

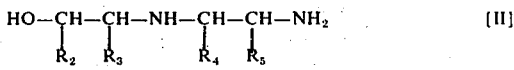

wherein:
$R_2$ – $R_5$ are either hydrogen or an unsubstituted or substituted aliphatic hydrocarbon radical having from two to six carbon atoms, which when substituted, preferably contains inert substituents such as lower alkyl or alkoxy, etc.; or other inert substituents such as Cl, Br, OH, OCH₃, etc. The preferred aminoalkyl alkanolamine is, as previously noted, aminoethyl ethanolamine.

Basic catalysts which are useful in amide formation in accordance with the present invention are the alkali metals, e.g., sodium, potassium, lithium, etc.; the corresponding alkali metal, or alkaline earth, hydroxides; alkali metal alkoxides; and quaternary ammonium hydroxides. The preferred base catalysts are sodium methoxide and trimethylbenzyl ammonium hydroxide.

The thus-formed tertiary monoamides can be recovered, but preferably they are not recovered, and the reaction product is directly carboxyalkylated by conventional means including reaction, for example, with a monohalocarboxylic acid or salt thereof — such as

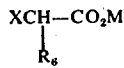

where X is halo (e.g., Cl or Br), $R_6$ is H or $C_1$–$C_4$ alkyl, and M is H, an alkali metal or ammonium — $ClCH_2CO_2H$ or $ClCH_2CO_2Na$, for example, either in the presence or absence of base. The preferred conditions of this carboxyalkylation reaction are shown, e.g., in the U.S. Pat. Nos. 2,961,451 and 2,970,160, whose disclosure in this regard is hereby incorporated herein by reference.

The products of carboxymethylation have been found to be improved amphoteric surface active compositions of the formula:

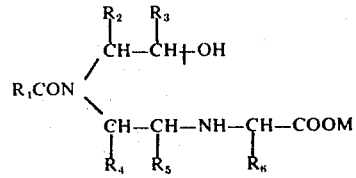

wherein $R_1$ is a substituted or unsubstituted $C_5$–$C_{29}$ hydrocarbon radical and $R_2$–$R_5$ are H, or substituted or unsubstituted $C_2$–$C_6$ radicals, which when substituted, can contain such substituents as Cl, Br, OH, OCH₃, etc.; $R_6$ is either H or a lower ($C_1$–$C_4$) alkyl group; and M is either H, or a metal atom such as an alkali metal, or ammonium.

The invention can be further illustrated by the following representative, non-limiting examples wherein are described how some of the compounds within the scope of the present invention can be made and used.

EXAMPLE I (Preparation of Tertiary Amide)

295 parts by weight (one mole) of a conventional commercial methyl ester of a fatty acid having an average of eighteen carbon atoms per molecule (CE 18/95), a proprietary product of Procter & Gamble having the following tabulated composition (Gas-Liquid Chromatography, %):

| Composition | Typical | Limit |
|---|---|---|
| $C_6$ | 1 | |
| $C_8$ | 9 | 7–9.5 |
| $C_{10}$ | 7 | 4–10 |
| $C_{12}$ | 49 | 44–49 |
| $C_{14}$ | 19 | 15–24 |
| $C_{16}$ | 7 | 5.5–10 |
| $C_{18}$ | 9 | 5–10 |
| Saponification Value | 255 | |
| Acid Value | 0.4 | 0.5 max. |
| Iodine Value | 11 | 14 max. |
| Unsaponifiable (%) | 0.1 | 0.2 max. |
| Moisture (%) | 0.07 | 0.1 max. |
| Average Molecular weight | 220 | |

Physical Properties

| | | |
|---|---|---|
| Specific Gravity 25/25°C | 0.864 | |
| Melting Point, °C | 4.0 | |
| Reflective Index ( ) | 1.4332 | |
| % Transmission (460m) | 95 | 90 min. |

104 parts by weight (one mole) of aminoethyl ethanolamine and 5 parts by weight of 25% methanolic sodium methoxide were placed in a glass reaction vessel equipped with a stirrer, a thermometer, a nitrogen inlet and an outlet tube connected to a vacuum system through a dry ice trap and manometer. The heterogeneous liquid mixture was gradually heated under 150 mm vacuum. As the temperature went to 60° – 70°C, methanol was rapidly given off and the heterogeneous mixture became a clear, single-phase liquid. The temperature was then raised to 100°–105°C and held there at 150 mm vacuum for fifteen minutes. At the end of this period about 34 parts by weight of methanol had been collected in the dry ice trap. The reaction product was a slightly yellow transparent gel at room temperature.

The IR spectrum of a sample of the reaction product indicated the following:

| Absorption (5.5–6.7 micron region only) | Product Identified |
|---|---|
| 6.15 very strong | tertiary amide plus small amount of secondary amide |
| 6.45 very weak | secondary amide |

The major absorption of 6.15 microns is due to C=O stretching in tertiary amide, while the weak 6.45 micron absorption indicates the presence of a small quantity of secondary amide in the structure. N-$C_{18}$ acyl, N-(2-aminoethyl) ethanolamine is, therefore, the major product to the above reaction:

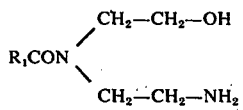

wherein $R_1$ is an acyclic $C_{17}$ fatty acid radical derived from CE 18/95 methyl ester, as noted above.

When the above material was heated at 100° to 105°C at 150 mm vacuum for another 35 minutes, no major change in IR spectrum occurred. Prolonged heating above 120°C, however, as previously indicated, causes slow rearrangement to the stable secondary amide and also simultaneous ring closure to an imidazoline structure.

EXAMPLE 2

(Preparation of Surface Active Agents)

367 parts by weight (one mole) of the reaction product of Example 1 were heated to 60°C in a glass reaction vessel fitted with a stirrer, a condenser and an additional funnel. A mixture of 200 parts by weight of water and 100 parts by weight of isopropanol were then added, and the clear resulting solution cooled at 45°C. A solution of 94.5 parts by weight (one mole) of monochloroacetic acid in 175 parts by weight water was then added to the above solution as rapidly as possible with external cooling so that the temperature did not exceed 55°C during additon. The resulting solution was again cooled to 45°C and 160 parts by weight of 50% aqueous NaOH (two moles NaOH) were added with external cooling at a rate such that the temperature did not exceed 55°C. This addition took about 10 minutes.

After addition of the reactants, the highly viscous reaction mixture was stirred at a slow rate for 3 hours between 50° and 60°C and then for 1 1/2 hours between 80°C and 90°C. During this time the pH of the reaction mixture dropped from 14 to 10.4. The product, which was light yellow semi-viscous paste at room temperature, can be represented by the formula:

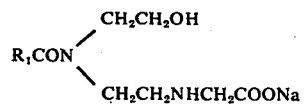

wherein:
$R_1$ is an acyclic $C_{17}$ fatty acid radical derived from CE 18/95 methyl ester, as previously identified in Example 1.

This product is useful as an amphoteric surfactant in a variety of applications and is particularly suitable as a shampoo composition.

EXAMPLE 3

The procedure of Example 1 was followed, except that 280 parts by weight of bleached tallow (a triglyceride) was substituted for the methyl ester of the eighteen carbon atom fatty acid, and the glycerol that formed during the reaction was allowed to remain in the reaction mixture. The IR spectrum of the product indicated virtually complete conversion to a tertiary monoamide contaminated with a small amount of the corresponding secondary amide. The product was then reacted with chloroacetic acid, as described in Example 2, to obtain the sodium salt of a carboxy methylated compound in which the fatty acid radical was the type found in tallow.

EXAMPLE 4

The procedure of Example 3 was repeated, except that only 40 parts by weight (one mole) of sodium hydroxide was used. The reaction product resulting was a white paste (pH=7) representing the internal salt of the free acid of the carboxy methylated compound of Example 3.

EXAMPLE 5

The procedure of Example 1 was repeated substituting 220 parts by weight (one mole) of the methyl ester of the fatty acids obtained from coconut oil, i.e., methyl cocoate, and utilizing 107 parts by weight (1.03 moles) of aminoethyl ethanolamine to obtain a tertiary amide having an acyl radical of the type obtained from coconut oil.

EXAMPLE 6

The tertiary amide obtained in Example 5 was dissolved in 200 parts by weight of water and the solution then was treated successively with (a) a solution of 94.5 parts by weight of chloroacetic acid in 175 parts by weight of water and (b) 160 parts by weight of 50% aqueous sodium hydroxide solution (two moles NaOH) following the procedure described with respect to Example 2, except that the isopropanol was not included in the reaction mixture. The product was a slightly viscous pale yellow solution (pH=10.5) and was miscible with water in all proportions. This product was the sodium salt of the carboxy methylated tertiary amide of Example 5 in which the fatty acid radical was of the type found in coconut vegetable oil.

EXAMPLE OF PREPARATION OF PRIOR ART SECONDARY AMINES (EXAMPLE 7)

220 parts by weight (one mole) of stripped coconut acid and 107 parts by weight (1.03 moles) of aminoethyl ethanolamine were condensed by placing in a glass reaction vessel equipped with a stirrer, a thermometer, a nitrogen inlet and an outlet tube connected to a vacuum system through a dry ice trap and a manometer. The reagents were mixed thoroughly at room temperature and then heated rapidly to 130°–140°C under 150 mm vacuum. A narrow stream of nitrogen was allowed to trickle in through the flask. The reaction mixture was heated at about 130° to 140°C at 150 mm vacuum for four hours with slow agitation. At the end of this period about 15 grams of liquid, mostly water, had collected in the dry ice trap. Analysis indicated the reaction product to be a secondary amide in about 75% conversion with about 25% of unreacted amine salt. The secondary amide was thus N-cocoacyl (2-hydroxyethyl) ethylenediamine. The condensate was then reacted with cloroacetic acid in the presence of sodium hydroxide, as in Example 6, to give the known surfactant N-cocoayl, N'-(2-hydroxyethyl), N'-carboxymethyl ethylenediamine, isolated as the sodium salt.

The reaction product of Example 7 was then compared with the reaction product of Example 6. For the purposes of comparison foaming properties of the reaction products were tested for foam height and foam stability at 80°F in distilled water by the Ross and Miles Foamometer Test (Ross, J. and Miles, G. D., Oil and Soap, 18, 99-102, 1941). The foaming properties of the reaction product of Example 6 were further compared, utilizing the Ross and Miles Foamometer Test with composition A, a well-known ampholyte which is widely used commercially as an imidazoline surfactant called Miranol C2M and has the following chemical structure:

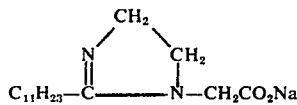

These results are shown in the following Table I.

TABLE 1

| Sample | Conc. Per cent | Foam Height in mm at 80°F in Distilled Water | |
|---|---|---|---|
| | | Initial | After 5 min. |
| Composition A | 0.05 | 160 | 140 |
| Example 6 | 0.05 | 140 | 125 |
| Composition A | 0.1 | 175 | 150 |
| Example 6 | 0.1 | 185 | 170 |
| Example 7 | 0.1 | 170 | 145 |
| Composition A | 0.5 | 200 | 175 |
| Example 6 | 0.5 | 220 | 200 |

From the information in Table 1 it can be seen that the reaction product of Example 6 is an excellent foaming agent that is equivalent to or better than composition A and somewhat superior than that of Example 7, insofar as foaming and foam stability are concerned.

The products of the current invention are thus useful as amphoteric surfactants typified by Examples 2, 3, 4 and 6, which surfactants are particularly useful as shampoos.

What I claim is:

1. A tertiary amide of the formula

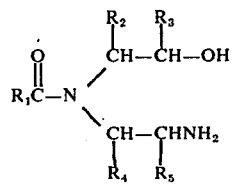

wherein:

$R_1$ is selected from the group consisting of unsubstituted $C_5-C_{29}$ and substituted $C_5-C_{29}$ aliphatic hydrocarbon radicals, which, when substituted, have one or more substituents selected from the group consisting of Cl, Br, OH and $OCH_3$; and $R_2-R_5$ are each selected from the group consisting of hydrogen unsubstituted $C_2-C_4$ aliphatic hydrocarbon radicals, and substituted $C_2-C_4$ aliphatic hydrocarbon radicals whose substituents are as previously defined for $R_1$.

2. Amides of claim 1 in which the acyl radical

is derived from tallow.

3. Amides of claim 1 in which the acyl radical

is a stearyl radical.

4. Amides of claim 1 in which the acyl radical

is derived from coconut vegetable oil.

5. A process for making tertiary amides of the formula as defined in claim 1, which comprises condensing a fatty acid ester having the acyl radical

and from 6 to 30 carbon atoms with a hydroxy diamine of the formula:

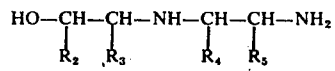

wherein: $R_2-R_5$ are as defined in claim 1, for from 5 minutes to an hour in the presence of a base catalyst and at a temperature between 60° and 120°C until the formation of the tertiary amide; and recovering the tertiary amide formed with the acyl radical

derived from said fatty acid ester.

6. The process of claim 5 in which said ester is the methyl ester.

7. The process of claim 5 in which said ester is a triglyceride.

8. The process of claim 5 in which said base catalyst is sodium methoxide.

9. The process of claim 6 in which methanol formed during the condensation of said ester and said hydroxy diamine is removed as said methanol is formed.

10. The process of claim 7 in which glycerol formed during condensation of said ester and said hydroxy diamine is left with the reaction product amide.

11. Amphoteric surface active agents of the formula:

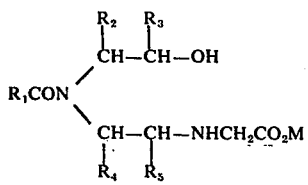

wherein $R_1$ is selected from the group consisting of unsubstituted $C_5$–$C_{29}$ and substituted $C_5$–$C_{29}$ aliphatic hydrocarbon radicals, which, when substituted, have one or more substituents selected from the group consisting of Cl, Br, OH and $OCH_3$; and $R_2$–$R_5$ are each selected from the group consisting of hydrogen, unsubstituted $C_2$–$C_4$ aliphatic hydrocarbon radicals, and substituted $C_2$–$C_4$ aliphatic hydrocarbon radicals whose substituents are as previously defined for $R_1$; and wherein M is selected from the group consisting of hydrogen, an alkali metal cation, and an ammonium cation.

12. An amphoteric surface active agent according to claim 11 having the formula:

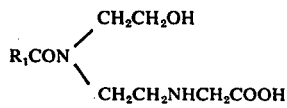

wherein the acyl radical $R_1CO$ is derived from hydrogenated tallow.

13. A process for making tertiary amide amphoteric surfactants of the formula defined in claim 11, which comprises condensing a fatty acid ester having from 6 to 30 carbon atoms with a hydroxy diamine of the formula:

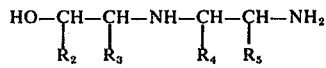

wherein:
$R_2$–$R_5$ are as defined in claim 1, for from 5 minutes to an hour in the presence of a base catalyst and at a temperature between 60° and 120°C, until formation of the tertiary amide, and reacting the reaction product containing said amide with an acidic material selected from the group consisting of

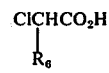

and salts thereof wherein $R_6$ is selected from the group consisting of hydrogen and $C_1$–$C_4$ alkyl to form said surfactants.

14. The process of claim 13 in which said fatty acid ester is an ester of a lower alcohol.

15. The process of claim 14 in which said ester is the methyl ester.

16. The process of claim 13 in which said ester is a triglyceride.

17. The process of claim 13 in which said base catalyst is sodium methoxide.

18. The process of claim 15 in which methanol formed during the condensation of said ester and said hydroxy diamine is removed as said methanol is formed.

19. The process of claim 16 in which glycerol formed during condensation of said ester and said hydroxy diamine is left with the reaction product amide.

* * * * *